United States Patent
Higgins et al.

(10) Patent No.: US 10,765,446 B2
(45) Date of Patent: Sep. 8, 2020

(54) SYSTEMS, METHODS AND DEVICES FOR REMOVAL OF THROMBUS AND/OR SOFT PLAQUE

(71) Applicant: Cardiovascular Systems, Inc., St. Paul, MN (US)

(72) Inventors: Joseph P. Higgins, Minnetonka, MN (US); Nicholas W. Rydberg, Stillwater, MN (US)

(73) Assignee: Cardiovascular Systems, Inc., St. Paul, MN (US)

( * ) Notice: Subject to any disclaimer, the term of this patent is extended or adjusted under 35 U.S.C. 154(b) by 240 days.

(21) Appl. No.: 15/865,346

(22) Filed: Jan. 9, 2018

(65) Prior Publication Data
US 2018/0235653 A1 Aug. 23, 2018

Related U.S. Application Data

(60) Provisional application No. 62/461,006, filed on Feb. 20, 2017.

(51) Int. Cl.
*A61B 17/22* (2006.01)
*A61B 17/3207* (2006.01)
*A61B 17/32* (2006.01)
*A61B 17/00* (2006.01)

(52) U.S. Cl.
CPC ........ *A61B 17/320758* (2013.01); *A61B 2017/00075* (2013.01); *A61B 2017/00685* (2013.01); *A61B 2017/22038* (2013.01); *A61B 2017/22079* (2013.01); *A61B 2017/320052* (2013.01); *A61B 2017/320775* (2013.01); *A61B 2217/005* (2013.01)

(58) Field of Classification Search
CPC .............. A61B 17/22; A61B 17/3207; A61B 17/22004; A61B 17/22031; A61B 17/320758; A61B 17/22012; A61B 2017/00075; A61B 17/22022
See application file for complete search history.

(56) References Cited

U.S. PATENT DOCUMENTS

| | | |
|---|---|---|
| 5,047,040 A | 9/1991 | Simpson et al. |
| 5,242,460 A | 9/1993 | Klein et al. |
| 5,507,795 A * | 4/1996 | Chiang .......... A61B 17/320783 606/167 |
| 2011/0213391 A1 | 9/2011 | Rivers et al. |

(Continued)

OTHER PUBLICATIONS

Notification Concerning Transmittal of International Preliminary Report on Patentability and International Preliminary Report on Patentability issued in related PCT application No. PCT/US2018/013316, dated Aug. 29, 2019.

(Continued)

*Primary Examiner* — Vi X Nguyen
(74) *Attorney, Agent, or Firm* — Barnes & Thornburg LLP; Jeffrey R. Stone

(57) ABSTRACT

A thrombectomy system is provided that, in various embodiments, a rotating impeller that may be translated within limits along a guidewire and within a catheter. The rotating impeller is, during operation, either located entirely outside of the distal end of the catheter's lumen or at least partially outside of the distal end of the catheter's lumen, whereby rotation is prevented if the impeller is completely within the catheter's lumen.

5 Claims, 3 Drawing Sheets

(56) References Cited

U.S. PATENT DOCUMENTS

2016/0287276 A1    10/2016  Cox et al.
2016/0374719 A1*   12/2016  Kessler .................. A61B 90/06
                                                        606/159

OTHER PUBLICATIONS

International Search Report and Written Opinion dated Mar. 28, 2018 issued in related PCT application No. PCT/US18/13316.

* cited by examiner

SYSTEMS, METHODS AND DEVICES FOR REMOVAL OF THROMBUS AND/OR SOFT PLAQUE

CROSS-REFERENCE TO RELATED APPLICATIONS

This application claims the benefit of U.S. Provisional Application No. 62/461,006, filed Feb. 20, 2017 and entitled SYSTEMS, METHODS AND DEVICES FOR REMOVAL OF THROMBUS AND/OR SOFT PLAQUE, the entirety of which is hereby incorporated by reference.

STATEMENT REGARDING FEDERALLY SPONSORED RESEARCH OR DEVELOPMENT

Not Applicable

BACKGROUND OF THE INVENTION

Field of the Invention

The invention relates to systems, devices and methods for removing thrombus and soft plaque material in an anatomical conduit. More specifically, a thrombectomy device and method that may be used in conjunction with adjunctive devices and methods such as atherectomy and/or angioplasty.

Description of the Related Art

A variety of techniques and instruments have been developed for use in the removal or repair of tissue in arteries and similar body passageways. A frequent objective of such techniques and instruments is the removal of atherosclerotic plaque in a patient's arteries. Atherosclerosis is characterized by the buildup of fatty deposits (atheromas) in the intimal layer (i.e., under the endothelium) of a patient's blood vessels. Very often over time what initially is deposited as relatively soft, cholesterol-rich atheromatous material hardens into a calcified atherosclerotic plaque. Such atheromas restrict the flow of blood, and therefore often are referred to as stenotic lesions or stenoses, the blocking material being referred to as stenotic material. If left untreated, such stenoses can cause angina, hypertension, myocardial infarction, strokes and the like.

In many cases, thrombus and/or soft plaque material must be removed. The presently described invention enables such removal and may be used in conjunction with an exchangeable handle or cartridge and adjunctive procedures such as, e.g., atherectomy and/or angioplasty procedures using the same exchangeable handle or cartridge.

Current thrombectomy devices tend to simply use suction to draw particles through a generic catheter. Often, these catheters become clogged with even moderately sized thrombus particles. Unclogging with current suction-based systems means using high pressure to dislodge the particles. This, in turn, leads to high levels of blood loss and added procedural risks.

Various embodiments of the present invention address these, inter alia, issues by, among other things, enabling a much lower aspiration pressure while allowing the physician to keep the device tip clear from clogging and enabling treatment of larger and longer regions or areas of thrombus or soft plaque.

BRIEF SUMMARY OF THE INVENTION

A thrombectomy system is provided that, in various embodiments, a rotating impeller that may be translated within limits along a guidewire and within a catheter. The rotating impeller is, during operation, either located entirely outside of the distal end of the catheter's lumen or at least partially outside of the distal end of the catheter's lumen.

The figures and the detailed description which follow more particularly exemplify these and other embodiments of the invention.

DETAILED DESCRIPTION OF THE INVENTION

Figure 1:
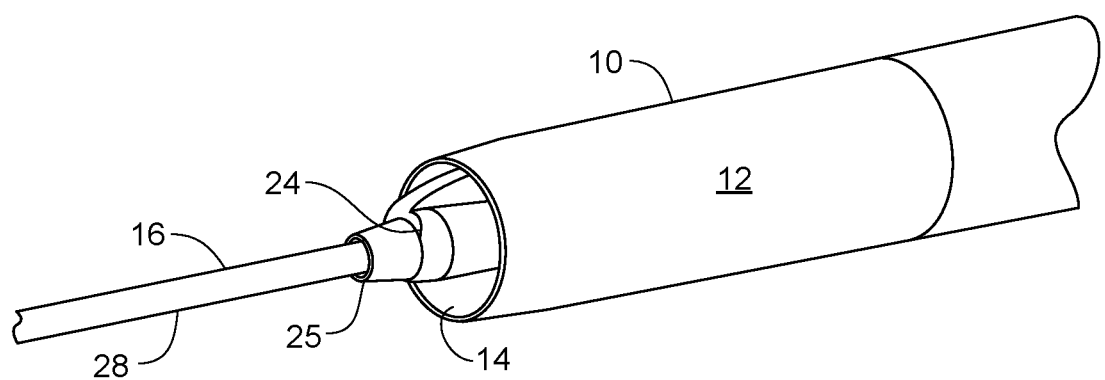
FIG. 1 is a perspective view of one embodiment of the present invention.

While the invention is amenable to various modifications and alternative forms, specifics thereof are shown by way of example in the drawings and described in detail herein. It should be understood, however, that the intention is not to limit the invention to the particular embodiments described. On the contrary, the intention is to cover all modifications, equivalents, and alternatives falling within the spirit and scope of the invention.

With reference to the Figures, one embodiment of the present invention comprising a catheter 10 having a body 12 with a distal end 15 and defining a lumen 14 therethrough. An impeller device 16 that is rotatable and translatable within catheter lumen 14 is provided and comprises a tubular shaft 18 defining a proximal end 20, a distal end 22 and an impeller 24 attached at or near the distal end 22 of the tubular shaft 18. A guidewire lumen 26 is defined through the impeller device, i.e., through the tubular shaft 18 and, in some cases, through the impeller 24 attached at or near the distal end 22 of the tubular shaft 18. The guidewire lumen 26 is adapted to receive a guidewire 28 therethrough, thereby enabling the impeller device 16 to be rotated as well as translated over the guidewire 28 and through the catheter lumen 106 to the treatment area in a blood vessel.

The impeller device 16 in FIG. 1 may be locked in place relative to the distal end 22 of the catheter body and the distal end of the catheter lumen 14, with a distal portion of the impeller 24 extending distally from of the distal end 22 of the catheter body 12, i.e., extending partially outside of the catheter lumen 106 to allow, inter alia, easy catheter insertion and enabling breakup of thrombus and/or soft plaque during insertion by rotating the impeller 24 during insertion and positioning of the catheter 12 and impeller device 16 to the location of interest.

Figure 4:
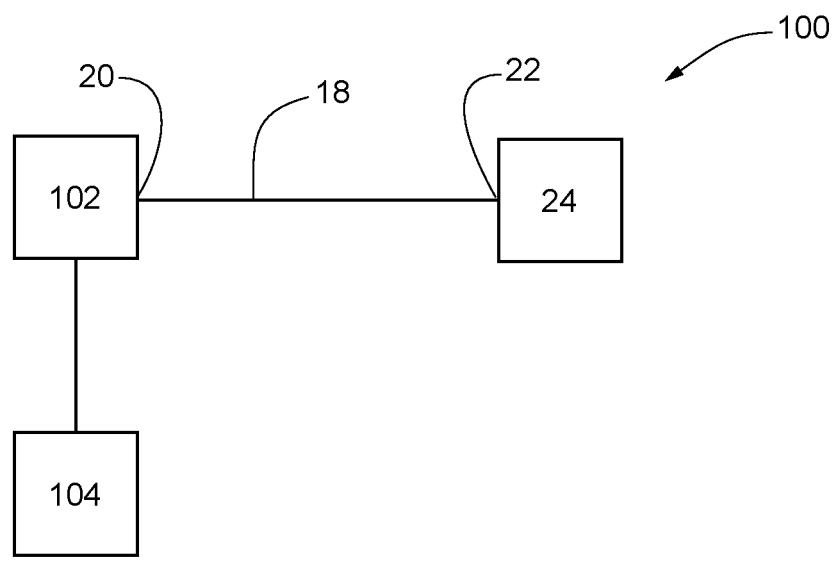
FIG. 4 is a schematic diagram of one embodiment of the present invention.

FIG. 4 illustrates a block schematic diagram of one embodiment of a thrombectomy system 100 comprising a prime mover 102, e.g., an electric motor or turbine or the equivalent in operative communication with a controller 104 comprising a processor in communication with a memory and a display and a data input such as a keyboard as is well known in the art. The prime mover 104 is in rotational connection with the tubular shaft 18 of the impeller device 16 which is, in turn, in attached communication with the impeller 24 as described above. The controller 104 comprises executable instructions stored therein, e.g., within the memory, that are executed by the processor. The executable instructions comprise at least (1) information about the length of the tubular shaft that is extended from the prime mover; (2) the distance of the distal tip 25 of the impeller 24 from the prime mover 102 along the tubular shaft 18; (3) instructions to prevent rotation of the prime mover 102, and thus the tubular shaft 18 and impeller 24 attached thereto, if the position of distal tip 25 of the impeller 24 within the lumen 106 of the catheter is completely within the lumen 106 and, therefore, does not extend beyond the distal end 15 of the catheter body 12; and (4) instructions to allow rotation of the prime mover 102, tubular shaft 18 and impeller 24 only if at least a portion of the impeller 24 extends distally away from the distal end 15 of the catheter body 10 and, therefore extending at least partially out of the catheter lumen 106.

Thus the embodiment in FIG. 1, with the impeller 24 at least partially extending distally beyond the catheter body 10 will, according to the above instructions, be allowed to rotate by the executable instructions of the controller 104.

The impeller 24 may comprise an elongated screw structure near or at its distal end that may have at least one elongated thread-like structure designed to macerate thrombus and/or soft tissue while also drawing the tissue/thrombus proximally toward the catheter where it may be aspirated therethrough.

Figure 2:
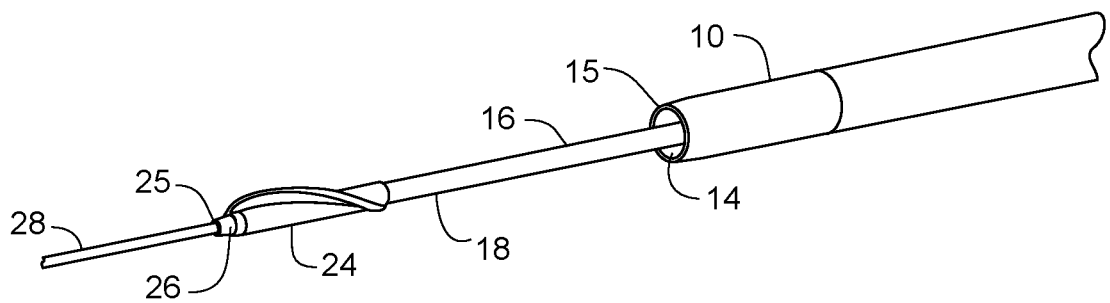
FIG. 2 is a perspective view of one embodiment of the present invention.

FIG. 2 illustrates the impeller device 16 and specifically the impeller 24 as translated distally out and away from the distal end 15 of the catheter 12 where it may macerate or break up soft plaque and/or thrombus, pulling it proximally after breakup toward the distal opening and lumen of the catheter for aspiration with continued rotation so long as at least a part of the impeller remains extended distally beyond the distal end 15 of the catheter 12 or catheter body 10.

Figure 3:
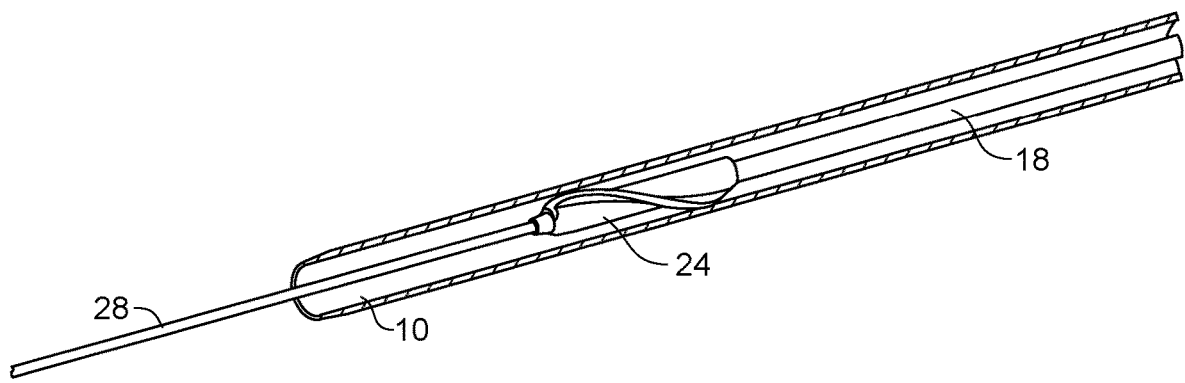
FIG. 3 is a perspective partial cutaway view of one embodiment of the present invention.

FIG. 3 illustrates the impeller device 16, including the impeller 24 positioned as translated proximally entirely within the lumen 14 of the catheter 12, with the impeller 24 spaced proximally from the distal end of the catheter. In this case, the executable instructions of the controller 104 prevent the impeller 24 from rotating.

Moreover, we provide disclosure of the following patents and applications, each of which are assigned to Cardiovascular Systems, Inc., and incorporated herein in their entirety, each of which may comprise systems, methods and/or devices that may be used with various embodiments of the presently disclosed subject matter:

U.S. Pat. No. 9,468,457, "ATHERECTOMY DEVICE WITH ECCENTRIC CROWN";

U.S. Pat. No. 9,439,674, "ROTATIONAL ATHERECTOMY DEVICE WITH EXCHANGEABLE DRIVE SHAFT AND MESHING GEARS";

U.S. Pat. No. 9,220,529, "ROTATIONAL ATHERECTOMY DEVICE WITH ELECTRIC MOTOR";

U.S. Pat. No. 9,119,661, "ROTATIONAL ATHERECTOMY DEVICE WITH ELECTRIC MOTOR";

U.S. Pat. No. 9,119,660, "ROTATIONAL ATHERECTOMY DEVICE WITH ELECTRIC MOTOR";

U.S. Pat. No. 9,078,692, "ROTATIONAL ATHERECTOMY SYSTEM";

U.S. Pat. No. 6,295,712, "ROTATIONAL ATHERECTOMY DEVICE";

U.S. Pat. No. 6,494,890, "ECCENTRIC ROTATIONAL ATHERECTOMY DEVICE";

U.S. Pat. No. 6,132,444, "ECCENTRIC DRIVE SHAFT FOR ATHERECTOMY DEVICE AND METHOD FOR MANUFACTURE";

U.S. Pat. No. 6,638,288, "ECCENTRIC DRIVE SHAFT FOR ATHERECTOMY DEVICE AND METHOD FOR MANUFACTURE";

U.S. Pat. No. 5,314,438, "ABRASIVE DRIVE SHAFT DEVICE FOR ROTATIONAL ATHERECTOMY";

U.S. Pat. No. 6,217,595, "ROTATIONAL ATHERECTOMY DEVICE";

U.S. Pat. No. 5,554,163, "ATHERECTOMY DEVICE";

U.S. Pat. No. 7,507,245, "ROTATIONAL ANGIOPLASTY DEVICE WITH ABRASIVE CROWN";

U.S. Pat. No. 6,129,734, "ROTATIONAL ATHERECTOMY DEVICE WITH RADIALLY EXPANDABLE PRIME MOVER COUPLING";

U.S. patent application Ser. No. 11/761,128, "ECCENTRIC ABRADING HEAD FOR HIGH-SPEED ROTATIONAL ATHERECTOMY DEVICES";

U.S. patent application Ser. No. 11/767,725, "SYSTEM, APPARATUS AND METHOD FOR OPENING AN OCCLUDED LESION";

U.S. patent application Ser. No. 12/130,083, "ECCENTRIC ABRADING ELEMENT FOR HIGH-SPEED ROTATIONAL ATHERECTOMY DEVICES";

U.S. patent application Ser. No. 12/363,914, "MULTI-MATERIAL ABRADING HEAD FOR ATHERECTOMY DEVICES HAVING LATERALLY DISPLACED CENTER OF MASS";

U.S. patent application Ser. No. 12/578,222, "ROTATIONAL ATHERECTOMY DEVICE WITH PRE-CURVED DRIVE SHAFT";

U.S. patent application Ser. No. 12/130,024, "ECCENTRIC ABRADING AND CUTTING HEAD FOR HIGH-SPEED ROTATIONAL ATHERECTOMY DEVICES";

U.S. patent application Ser. No. 12/580,590, "ECCENTRIC ABRADING AND CUTTING HEAD FOR HIGH-SPEED ROTATIONAL ATHERECTOMY DEVICES";

U.S. patent application Ser. No. 29/298,320, "ROTATIONAL ATHERECTOMY ABRASIVE CROWN";

U.S. patent application Ser. No. 29/297,122, "ROTATIONAL ATHERECTOMY ABRASIVE CROWN";

U.S. patent application Ser. No. 12/466,130, "BIDIRECTIONAL EXPANDABLE HEAD FOR ROTATIONAL ATHERECTOMY DEVICE"; and U.S. patent application Ser. No. 12/388,703, "ROTATIONAL ATHERECTOMY SEGMENTED ABRADING HEAD AND METHOD TO IMPROVE ABRADING EFFICIENCY".

The descriptions of the embodiments and their applications as set forth herein should be construed as illustrative, and are not intended to limit the scope of the disclosure. Features of various embodiments may be combined with other embodiments and/or features thereof within the metes and bounds of the disclosure. Upon study of this disclosure, variations and modifications of the embodiments disclosed herein are possible and practical alternatives to and equivalents of the various elements of the embodiments will be understood by and become apparent to those of ordinary skill in the art. Such variations and modifications of the embodiments disclosed herein may be made without departing from the scope and spirit of the invention. Therefore, all alternatives, variations, modifications, etc., as may become to one of ordinary skill in the art are considered as being within the metes and bounds of the instant disclosure.

What is claimed is:

1. A thrombus disruption and removal system comprising:
a catheter comprising a body defining a proximal end, a distal end and a lumen therebetween;

a tubular shaft defining a proximal end, a distal end, an impeller attached near the distal end of the tubular shaft and configured to draw soft plaque and/or thrombus proximally toward the lumen of the catheter after disruption, and a guidewire lumen defined through the tubular shaft and the impeller;

a prime mover coupled to the proximal end of the tubular shaft and adapted to rotate the impeller and to translate the impeller relative to the distal end of the catheter body;

a controller in operational communication with the prime mover and adapted to determine the translational position of the impeller, whereby the controller prevents rotation of the prime mover and the impeller if the impeller is not at least partially outside the lumen of the catheter and extending distally away from the distal end of the catheter body.

2. The system of claim 1, wherein the impeller further comprises an elongated screw structure.

3. The system of claim 1, wherein the impeller further comprises a helical structure.

4. The system of claim 1, wherein the impeller may be translated proximally or distally over a guide wire within an established distance limit.

5. A thrombus disruption and removal system comprising:
a catheter comprising a body defining a proximal end, a distal end and a lumen therebetween;

a tubular shaft defining a proximal end, a distal end, an impeller attached near the distal end of the tubular shaft, the impeller comprising an elongated screw structure, and a guidewire lumen defined through the tubular shaft and the impeller;

a prime mover coupled to the proximal end of the tubular shaft and adapted to rotate the impeller and to translate the impeller relative to the distal end of the catheter body;

a controller in operational communication with the prime mover and adapted to determine the translational position of the impeller, whereby the controller prevents rotation of the prime mover and the impeller if the impeller is not at least partially outside the lumen of the catheter and extending distally away from the distal end of the catheter body.

* * * * *